(12) United States Patent
Takahashi

(10) Patent No.: US 10,765,295 B2
(45) Date of Patent: Sep. 8, 2020

(54) IMAGE PROCESSING APPARATUS FOR DETECTING MOTION BETWEEN TWO GENERATED MOTION DETECTION IMAGES BASED ON IMAGES CAPTURED AT DIFFERENT TIMES, METHOD FOR OPERATING SUCH IMAGE PROCESSING APPARATUS, COMPUTER-READABLE RECORDING MEDIUM, AND ENDOSCOPE DEVICE

(71) Applicant: OLYMPUS CORPORATION, Tokyo (JP)

(72) Inventor: Jumpei Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 560 days.

(21) Appl. No.: 15/639,526

(22) Filed: Jun. 30, 2017

(65) Prior Publication Data

US 2017/0296033 A1    Oct. 19, 2017

Related U.S. Application Data

(63) Continuation of application No. PCT/JP2015/051427, filed on Jan. 20, 2015.

(51) Int. Cl.
*A61B 1/00* (2006.01)
*A61B 1/04* (2006.01)
(Continued)

(52) U.S. Cl.
CPC ............ *A61B 1/00009* (2013.01); *A61B 1/04* (2013.01); *A61B 1/0638* (2013.01);
(Continued)

(58) Field of Classification Search
CPC .................................................... A61B 1/0638
See application file for complete search history.

(56) References Cited

U.S. PATENT DOCUMENTS

| 2011/0019035 A1* | 1/2011 | Satodate ................ H04N 5/357 |
| | | 348/241 |
| 2012/0116159 A1* | 5/2012 | Mizuyoshi ........... A61B 1/0638 |
| | | 600/109 |

(Continued)

FOREIGN PATENT DOCUMENTS

| JP | 2005-150903 A | 6/2005 |
| JP | 2011-010998 A | 1/2011 |

(Continued)

OTHER PUBLICATIONS

康孝 松尾澄男 矢野, English Translation JP4630174, Feb. 2011, p. 1-8. (Year: 2011).*

(Continued)

*Primary Examiner* — Gandhi Thirugnanam
(74) *Attorney, Agent, or Firm* — Scully Scott Murphy & Presser

(57) ABSTRACT

An image processing apparatus configured to perform averaging processing on pixel values of pixels having different color filters to obtain a signal value, and generate motion detection images based on the signal value in such a way that, in WLI, a weight of a pixel value for a filter for passing light of a luminance component of a captured image in WLI is set to be larger than or equal to a weight of a pixel value for a different filter while in NBI, a weight of a pixel value for a filter for passing light of a luminance component of a captured image in NBI is set to be larger than or equal to a weight of a pixel value for a different filter. Based on the captured images at different points in time, the image (Continued)

processing apparatus detects motion between two of the generated motion detection images.

7 Claims, 15 Drawing Sheets

(51) Int. Cl.
*H04N 9/04* (2006.01)
*H04N 5/225* (2006.01)
*H04N 5/232* (2006.01)
*A61B 1/06* (2006.01)

(52) U.S. Cl.
CPC ........... *A61B 1/0646* (2013.01); *H04N 5/225* (2013.01); *H04N 5/2256* (2013.01); *H04N 5/232* (2013.01); *H04N 9/04* (2013.01); *H04N 2005/2255* (2013.01)

(56) References Cited

U.S. PATENT DOCUMENTS

| | | | | |
|---|---|---|---|---|
| 2012/0127292 A1* | 5/2012 | Yamazaki | ............ | A61B 1/0638 348/68 |
| 2012/0127293 A1* | 5/2012 | Yamazaki | .......... | A61B 1/00009 348/71 |
| 2012/0218394 A1* | 8/2012 | Yoshino | ............... | A61B 1/0638 348/65 |
| 2012/0220840 A1* | 8/2012 | Morita | ................. | A61B 1/0638 600/317 |
| 2012/0271103 A1* | 10/2012 | Gono | ................... | A61B 1/0684 600/109 |
| 2015/0363942 A1* | 12/2015 | Mitsui | ...................... | A61B 1/05 348/65 |
| 2016/0278613 A1* | 9/2016 | Kuriyama | ............... | A61B 1/005 |
| 2017/0055816 A1* | 3/2017 | Takahashi | .......... | G02B 23/2484 |
| 2017/0243325 A1* | 8/2017 | Sasaki | .................. | A61B 1/0638 |
| 2017/0251915 A1* | 9/2017 | Takahashi | ............ | A61B 1/0653 |
| 2017/0296033 A1* | 10/2017 | Takahashi | ............ | A61B 1/0646 |

FOREIGN PATENT DOCUMENTS

| | | |
|---|---|---|
| JP | 2011-029722 A | 2/2011 |
| JP | 4630174 B2 * | 2/2011 |
| JP | 4630174 B2 | 2/2011 |
| JP | 2012-157383 A | 8/2012 |

OTHER PUBLICATIONS

International Search Report dated Mar. 31, 2015 issued in PCT/JP2015/051427.

English abstract of Japanese Publication No. 2007-133823.

* cited by examiner

| P00 | P10 | P20 | P30 | ... |
|-----|-----|-----|-----|-----|
| P01 | P11 | P21 | P31 | ... |
| P02 | P12 | P22 | P32 | ... |
| P03 | P13 | P23 | P33 | ... |
| ⋮ | ⋮ | ⋮ | ⋮ | ⋱ |

FIG.9

| Y(0,0) | Y(1,0) | Y(2,0) | Y(3,0) | ⋯ |
|---|---|---|---|---|
| Y(0,1) | Y(1,1) | Y(2,1) | Y(3,1) | ⋯ |
| Y(0,2) | Y(1,2) | Y(2,2) | Y(3,2) | ⋯ |
| Y(0,3) | Y(1,3) | Y(2,3) | Y(3,3) | ⋯ |
| ⋮ | ⋮ | ⋮ | ⋮ | ⋱ |

FIG.10

| G(0,0) | R(1,0) | G(2,0) | R(3,0) | ⋯ |
|---|---|---|---|---|
| B(0,1) | G(1,1) | B(2,1) | G(3,1) | ⋯ |
| G(0,2) | R(1,2) | G(2,2) | R(3,2) | ⋯ |
| B(0,3) | G(1,3) | B(2,3) | G(3,3) | ⋯ |
| ⋮ | ⋮ | ⋮ | ⋮ | ⋱ |

FIG.12A

|  | Sg1 | Sb1 |  |  |
|---|---|---|---|---|
| G(0,0) | R(1,0) | G(2,0) | R(3,0) | ... |
| B(0,1) | G(1,1) | B(2,1) | G(3,1) | ... |
| G(0,2) | R(1,2) | G(2,2) | R(3,2) | ... |
| B(0,3) | G(1,3) | B(2,3) | G(3,3) | ... |
| ⋮ | ⋮ | ⋮ | ⋮ | ⋱ |

FIG.12B

|  | Sb2 | Sg2 |  |  |
|---|---|---|---|---|
| G(0,0) | R(1,0) | G(2,0) | R(3,0) | ... |
| B(0,1) | G(1,1) | B(2,1) | G(3,1) | ... |
| G(0,2) | R(1,2) | G(2,2) | R(3,2) | ... |
| B(0,3) | G(1,3) | B(2,3) | G(3,3) | ... |
| ⋮ | ⋮ | ⋮ | ⋮ | ⋱ |

FIG.13

| | | | | |
|---|---|---|---|---|
| G(0,0) | R(1,0) | G(2,0) | R(3,0) | ... |
| B(0,1) | G(1,1) | B(2,1) | G(3,1) | ... |
| G(0,2) | R(1,2) | G(2,2) | R(3,2) | ... |
| B(0,3) | G(1,3) | B(2,3) | G(3,3) | ... |
| : | : | : | : | ⋱ |

| | | | | |
|---|---|---|---|---|
| G(0,0) | R(1,0) | G(2,0) | R(3,0) | ... |
| B(0,1) | G(1,1) | B(2,1) | G(3,1) | ... |
| G(0,2) | R(1,2) | G(2,2) | R(3,2) | ... |
| B(0,3) | G(1,3) | B(2,3) | G(3,3) | ... |
| : | : | : | : | ⋱ |

| G(0,0) | R(1,0) | G(2,0) | R(3,0) | ⋯ |
|---|---|---|---|---|
| B(0,1) | G(1,1) | B(2,1) | G(3,1) | ⋯ |
| G(0,2) | R(1,2) | G(2,2) | R(3,2) | ⋯ |
| B(0,3) | G(1,3) | B(2,3) | G(3,3) | ⋯ |
| ⋮ | ⋮ | ⋮ | ⋮ | ⋱ |

| G(0,0) | R(1,0) | G(2,0) | R(3,0) | ⋯ |
|---|---|---|---|---|
| B(0,1) | G(1,1) | B(2,1) | G(3,1) | ⋯ |
| G(0,2) | R(1,2) | G(2,2) | R(3,2) | ⋯ |
| B(0,3) | G(1,3) | B(2,3) | G(3,3) | ⋯ |
| ⋮ | ⋮ | ⋮ | ⋮ | ⋱ |

| G(0,0) | R(1,0) | G(2,0) | R(3,0) | ... |
|---|---|---|---|---|
| B(0,1) | G(1,1) | B(2,1) | G(3,1) | ... |
| G(0,2) | R(1,2) | G(2,2) | R(3,2) | ... |
| B(0,3) | G(1,3) | B(2,3) | G(3,3) | ... |
| G(0,4) | R(1,4) | G(2,4) | R(3,4) | ... |
| ⋮ | ⋮ | ⋮ | ⋮ | ⋱ |

Q31, Q32

⇒

| Ys(0,0) | Ys(1,0) | ... |
|---|---|---|
| Ys(0,1) | Ys(1,1) | ... |
| ⋮ | ⋮ | ⋱ |

| G(0,0) | R(1,0) | G(2,0) | R(3,0) | ... |
|---|---|---|---|---|
| B(0,1) | G(1,1) | ●B(2,1) | G(3,1) | ... |
| G(0,2) | R(1,2) | G(2,2) | R(3,2) | ... |
| B(0,3) | G(1,3) | B(2,3) | G(3,3) | ... |
| ⋮ | ⋮ | ⋮ | ⋮ | ⋱ |

FIG.22

| G(0,0) | R(1,0) | G(2,0) | R(3,0) | ·· |
|---|---|---|---|---|
| B(0,1) | G(1,1) | B(2,1) | G(3,1) | ··· |
| G(0,2) | R(1,2) | G(2,2) | R(3,2) | ··· |
| B(0,3) | G(1,3) | ● B(2,3) | G(3,3) | ··· |
| G(0,4) | R(1,4) | G(2,4) | R(3,4) | ··· |
| ⋮ | ⋮ | ⋮ | ⋮ | ⋱ |

| $G_{00}$ | $B_{10}$ | $G_{20}$ | $R_{30}$ | ··· |
|---|---|---|---|---|
| $B_{01}$ | $G_{11}$ | $B_{21}$ | $G_{31}$ | ··· |
| $G_{02}$ | $R_{12}$ | $G_{22}$ | $B_{32}$ | ··· |
| $B_{03}$ | $G_{13}$ | $B_{23}$ | $G_{33}$ | ··· |
| ⋮ | ⋮ | ⋮ | ⋮ | ⋱ |

IMAGE PROCESSING APPARATUS FOR DETECTING MOTION BETWEEN TWO GENERATED MOTION DETECTION IMAGES BASED ON IMAGES CAPTURED AT DIFFERENT TIMES, METHOD FOR OPERATING SUCH IMAGE PROCESSING APPARATUS, COMPUTER-READABLE RECORDING MEDIUM, AND ENDOSCOPE DEVICE

CROSS REFERENCES TO RELATED APPLICATIONS

This application is a continuation of PCT international application Ser. No. PCT/JP2015/051427, filed on Jan. 20, 2015 which designates the United States, incorporated herein by reference.

BACKGROUND

1. Technical Field

The disclosure relates to an image processing apparatus for performing signal processing on an imaging signal generated by an image sensor to generate an image signal. The disclosure also relates to a method for operating the image processing apparatus, a computer-readable recording medium, and an endoscope device including the image processing apparatus.

2. Related Art

In the related art, endoscope devices have been widely used for various tests in the medical field and the industrial field. Of these, endoscope devices for medical use have been popular since they are capable of acquiring in-vivo images of a subject without incising the subject by inserting, into the subject such as a patient, an elongated flexible insertion unit provided with an image sensor including a plurality of pixels at a distal end thereof, thereby placing less burden on the subject.

As imaging methods of such endoscope devices, a white light imaging (WLI) using white illumination light and a narrow band imaging (NBI) using illumination light formed by two types of narrow band light (narrow band illumination light) each included in a blue and a green wavelength band are already widely known in the concerned technical field. Regarding such imaging methods of endoscope devices, it is desired to perform observation while switching between the white light imaging (WLI mode) and the narrow band imaging (NBI mode). The WLI mode has characteristics that biological structures (blood vessels, mucosa, etc.) important for diagnosis are depicted by a signal of a green component (G signal). Contrarily, the NBI mode has characteristics that biological structures are depicted by a signal of a blue component (B signal).

In order to generate and display a color image by the imaging method described above, a color filter, where a plurality of filters is arranged in a matrix form in the unit of a filter array that is generally called a Bayer array, is provided on a light-receiving surface of an image sensor to acquire an captured image by the image sensor of a single plate. The Bayer array is formed by arranging four filters for passing light of wavelength bands of red (R), green (G), green (G), and blue (B), respectively, in 2×2 in which the G filters for passing light of a green wavelength band arranged diagonally. Each of the pixels receives light of a wavelength band passed through the filter and the image sensor generates an electric signal of a color component corresponding to color of that wavelength band.

As technique to reduce noise included in a color image, an image processing apparatus which detects a motion vector between temporally continuous images and reduces the noise in the image according to the detected motion vector is known (e.g. see JP 2005-150903 A).

As technique to detect a motion vector between images generated using an image sensor provided with a color filter of the Bayer array, a motion vector detecting device which detects a motion vector using a luminance signal (Y signal) generated by deriving an arithmetic mean of four color signals generated by the Bayer array (e.g. see Japanese Patent No. 4630174).

SUMMARY

In some embodiments, provided is an image processing apparatus for generating a captured image based on a signal value generated by a plurality of pixels according to one of white illumination light in white light imaging and narrow band illumination light in a narrow band light imaging, the white illumination light including red, green, and blue wavelength bands, the narrow band illumination light being included in one of the red, green, and blue wavelength bands. The image processing apparatus includes: a motion detection image generating unit configured to perform averaging processing on pixel values of pixels included in a group of a plurality of pixels having different color filters to obtain a signal value for generating motion detection images, and generate the motion detection images for detecting motion between captured images at different points in time based on the signal value obtained by the averaging processing in such a way that, in the white light imaging, a weight of a pixel value of a pixel having a filter for passing light of a luminance component of a captured image in the white light imaging is set to be larger than or equal to a weight of a pixel value of a pixel having a different type of filter while in the narrow band imaging, a weight of a pixel value of a pixel having a filter for passing light of a luminance component of a captured image in the narrow band imaging is set to be larger than or equal to a weight of a pixel value of a pixel having a different type of filter; and a motion detection processing unit configured to detect, based on the motion detection images generated by the motion detection image generating unit, the motion between two of the motion detection images generated based on the captured images at the different points in time.

In some embodiments, provided is a method for operating an image processing apparatus for generating a captured image based on a signal value generated by a plurality of pixels according to one of white illumination light in white light imaging and narrow band illumination light in a narrow band light imaging, the white illumination light including red, green, and blue wavelength bands, the narrow band illumination light being included in one of the red, green, and blue wavelength bands. The method includes: performing, by a motion detection image generating unit, averaging processing on pixel values of pixels included in a group of a plurality of pixels having different color filters to obtain a signal value for generating motion detection images, and generating the motion detection images for detecting motion between captured images at different points in time based on the signal value obtained by the averaging processing in such a way that, in the white light imaging, a weight of a pixel value of a pixel having a filter for passing light of a luminance component of a captured image in the white light imaging is set to be larger than or equal to a weight of a pixel value of a pixel having a different type of filter while in the narrow band imaging, a weight of a pixel value of a pixel having a filter for passing light of a luminance component of a captured image in the narrow band imaging is set to be larger than or equal to a weight of a pixel value of a pixel having a different type of filter; and detecting, by a motion detection processing unit, based on the motion detection images generated by the motion detection image generating unit, the motion between two of the motion detection images generated based on the captured images at the different points in time.

In some embodiments, provided is a non-transitory computer-readable recording medium with an executable program stored thereon for operating an image processing apparatus for generating a captured image based on a signal value generated by a plurality of pixels according to one of white illumination light in white light imaging and narrow band illumination light in a narrow band light imaging, the white illumination light including red, green, and blue wavelength bands, the narrow band illumination light being included in one of the red, green, and blue wavelength bands. The program causes the image processing apparatus to execute: performing, by a motion detection image generating unit, averaging processing on pixel values of pixels included in a group of a plurality of pixels having different color filters to obtain a signal value for generating motion detection images, and generating the motion detection images for detecting motion between captured images at different points in time based on the signal value obtained by the averaging processing in such a way that, in the white light imaging, a weight of a pixel value of a pixel having a filter for passing light of a luminance component of a captured image in the white light imaging is set to be larger than or equal to a weight of a pixel value of a pixel having a different type of filter while in the narrow band imaging, a weight of a pixel value of a pixel having a filter for passing light of a luminance component of a captured image in the narrow band imaging is set to be larger than or equal to a weight of a pixel value of a pixel having a different type of filter; and detecting, by a motion detection processing unit, based on the motion detection images generated by the motion detection image generating unit, the motion between two of the motion detection images generated based on the captured images at the different points in time.

In some embodiments, provided is an endoscope device for performing white light imaging and narrow band light imaging. The endoscope device includes: a light source unit configured to emit one of white illumination light and narrow band illumination light, the white illumination light including red, green, and blue wavelength bands, the narrow band illumination light including two narrow bands included in one of wavelength bands of luminance components in the white light imaging and the narrow band light imaging; an image sensor having a plurality of pixels arranged in a matrix form, the plurality of pixels being configured to receive light and perform photoelectric conversion on the received light to generate an electric signal; a color filter having a plurality of filter units arranged on a light-receiving surface of the image sensor, each of the plurality of filter units including a first filter, a second filter, and a third filter, the first filter being configured to pass light of wavelength bands of a luminance component in the white light imaging and a luminance component in the narrow band light imaging, the second filter being configured to pass light of a wavelength band of the luminance component in the white light imaging, and the third filter being configured to pass light of a wavelength band of the luminance component in the narrow band light imaging; and the image processing apparatus.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a diagram explaining motion detection image generating processing performed by the motion detection image generating processing unit of the endoscope device according to the embodiment of the present invention;

FIG. 10 is a diagram explaining motion detection image generating processing performed by the motion detection image generating processing unit of the endoscope device according to the embodiment of the present invention;

FIG. 12A is a diagram explaining motion detection image generating processing performed by the motion detection image generating processing unit of the endoscope device according to the embodiment of the present invention;

FIG. 12B is a diagram explaining motion detection image generating processing performed by the motion detection image generating processing unit of the endoscope device according to the embodiment of the present invention;

FIG. 13 is a diagram explaining motion detection image generating processing performed by the motion detection image generating processing unit of the endoscope device according to the embodiment of the present invention;

FIG. 14 is a diagram explaining motion detection image generating processing performed by the motion detection image generating processing unit of the endoscope device according to the embodiment of the present invention;

FIG. 15 is a diagram explaining motion detection image generating processing performed by the motion detection image generating processing unit of the endoscope device according to the embodiment of the present invention;

FIG. 16 is a diagram explaining motion detection image generating processing performed by the motion detection image generating processing unit of the endoscope device according to the embodiment of the present invention;

FIG. 20 is a diagram explaining motion detection image generating processing performed by the motion detection image generating processing unit of the endoscope device according to the fourth modification of the embodiment of the present invention;

FIG. 21 is a diagram explaining motion detection image generating processing performed by the motion detection image generating processing unit of the endoscope device according to the fourth modification of the embodiment of the present invention;

FIG. 22 is a diagram explaining motion detection image generating processing performed by the motion detection image generating processing unit of the endoscope device according to the fourth modification of the embodiment of the present invention; and FIG. 23 is a schematic diagram illustrating a configuration of a color filter according to a fifth modification of the embodiment of the present invention.

DETAILED DESCRIPTION

Exemplary embodiments of the present invention will be described below. In the embodiments, as an exemplary device including an image processing apparatus, reference will be made to an endoscope device for medical use that captures and display in-vivo images of a patient or the like. The present invention is not limited by the embodiments. The same reference signs are used to designate the same elements throughout the drawings.

Embodiments

Figure 1:
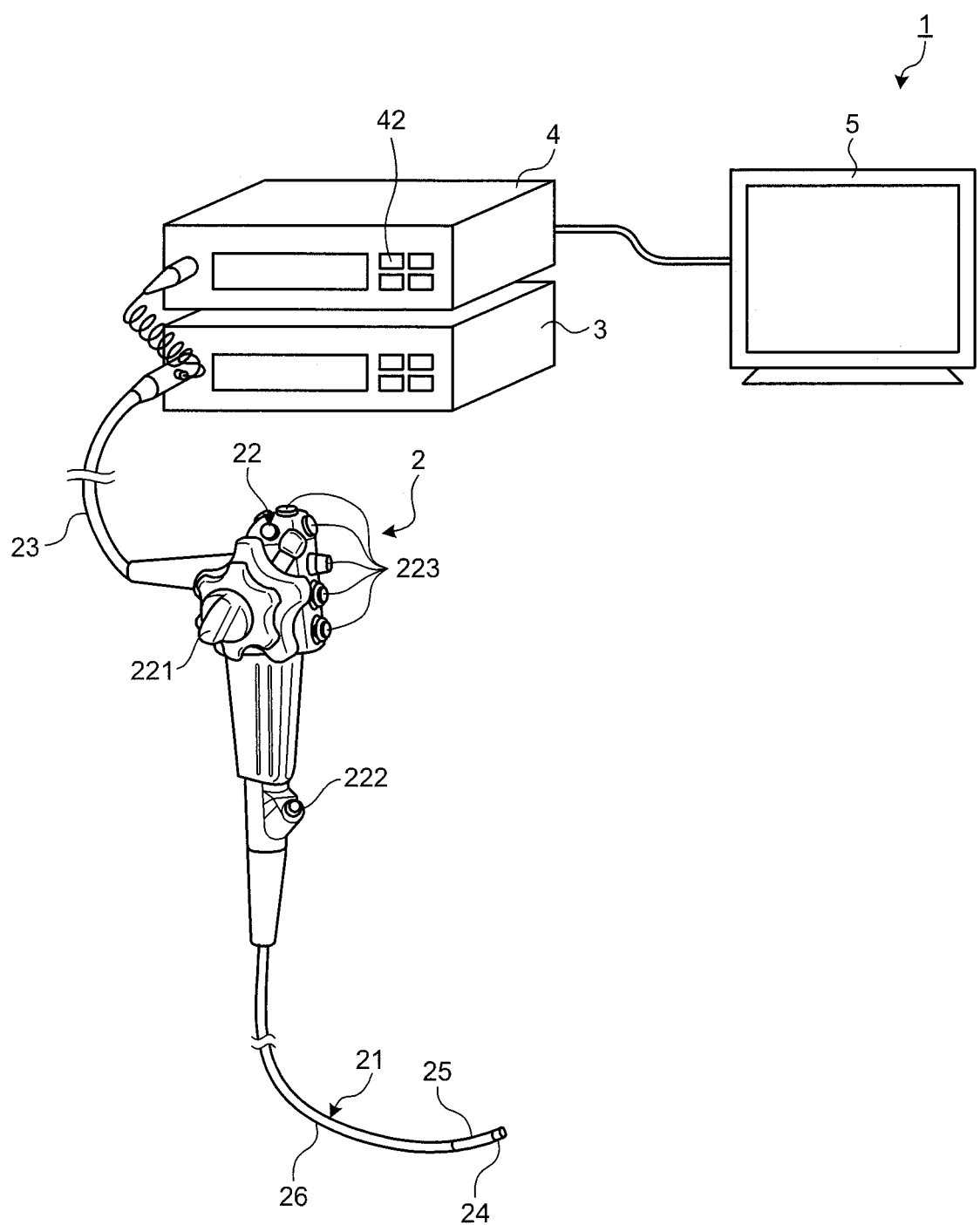
FIG. 1 is a diagram illustrating a schematic configuration of an endoscope device according to an embodiment of the present invention.
Figure 2:
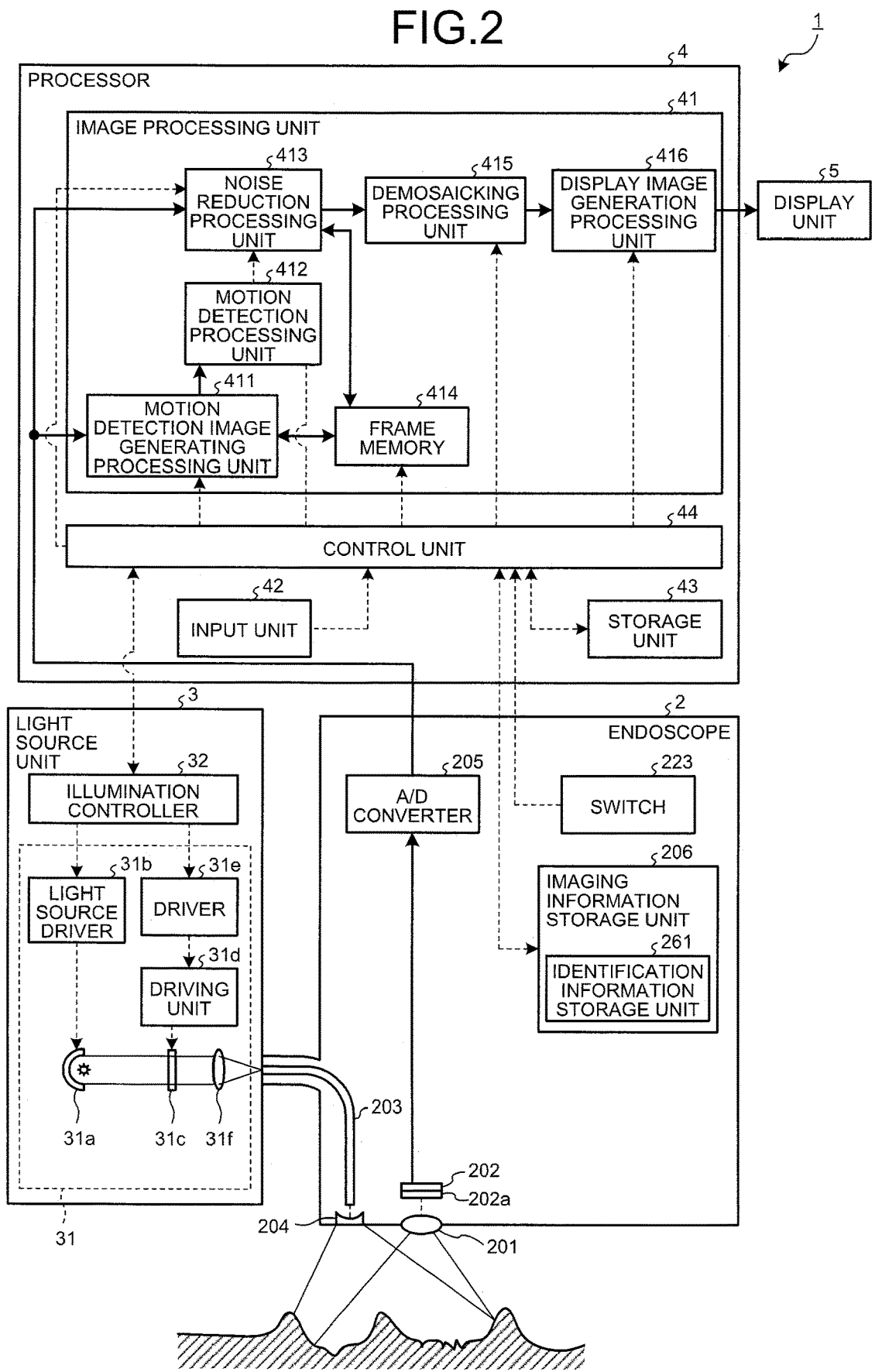
FIG. 2 is a schematic diagram illustrating a schematic configuration of the endoscope device according to the embodiment of the present invention.

FIG. 1 is a diagram illustrating a schematic configuration of an endoscope device 1 according to an embodiment of the present invention. FIG. 2 is a schematic diagram illustrating a schematic configuration of the endoscope device 1 according to the embodiment of the present invention. An endoscope device 1 illustrated in FIGS. 1 and 2 includes: an endoscope 2 that captures an in-vivo image of an observed region by insertion of an insertion unit 21 in a subject and generates an electric signal; a light source unit 3 that generates illumination light to be emitted from a distal end of the endoscope 2; a processor 4 that performs predetermined image processing on the electric signal acquired by the endoscope 2 and performs overall control of the endoscope device 1; and a display unit 5 that displays the in-vivo image on which the image processing has been performed by the processor 4. The endoscope device 1 acquires an in-vivo image in a subject by insertion of the insertion unit 21 in the subject such as a patient. An operator such as a doctor observes the acquired in-vivo image and thereby examines whether there is a bleeding site or a tumor site to be detected.

The endoscope 2 includes: the insertion unit 21 that is flexible and elongated; an operating unit 22 connected to a proximal end side of the insertion unit 21 and receives input of various operation signals; and a universal cord 23 extending in a different direction from a direction in which the insertion unit 21 extends from the operating unit 22 and incorporates various cables connected to the light source unit 3 and the processor 4.

The insertion unit 21 includes: a distal end part 24 incorporating an image sensor 202 in which pixels (photodiodes) for receiving light and performing photoelectric conversion on the received light to generate an image signal are arranged in a matrix form; a bending part 25 that is bendable and formed by a plurality of bending pieces; and an elongated flexible tube part 26 connected to a proximal end side of the bending part 25.

The operating unit 22 includes: a bending knob 221 that causes the bending part 25 to bend in the vertical direction and the horizontal direction; a treatment tool insertion unit 222 for inserting a treatment tool, such as forceps, an electric scalpel, and an inspection probe, into a subject; and a plurality of switches 223 for inputting a command signal for causing the light source unit 3 to perform switching operation of illumination light, an operation command signal for an external device connected to a treatment tool or the processor 4, a water supply command signal for supplying water, a suction command signal for performing suction, or other command signals. A treatment tool inserted from the treatment tool insertion unit 222 is exposed from an opening part (not illustrated) via a treatment tool channel (not illustrated) included in a distal end of the distal end part 24.

The universal cord 23 incorporates at least a light guide 203 and a collective cable where one or more signal wires are bundled. The collective cable includes signal wires for transmitting and receiving a signal to and from the endoscope 2, the light source unit 3, and the processor 4 including a signal wire for transmitting and receiving setting data, a signal wire for transmitting and receiving an image signal, a signal wire for transmitting and receiving a timing signal for driving the image sensor 202, and other signal wires.

The endoscope 2 includes an imaging optical system 201, the image sensor 202, the light guide 203, an illumination lens 204, an A/D converter 205, and an imaging information storage unit 206.

The imaging optical system 201 is provided to the distal end part 24 and concentrates light at least from an observed region. The imaging optical system 201 is formed by one or more lenses. The imaging optical system 201 may be provided with an optical zoom mechanism that changes the angle of view and a focus mechanism that changes the focus.

The image sensor 202 is disposed vertically with respect to an optical axis of the imaging optical system 201 and generates an electric signal (image signal) by photoelectric conversion of an image of light formed by the imaging optical system 201. The image sensor 202 is implemented by using a charge coupled device (CCD) image sensor, a complementary metal oxide semiconductor (CMOS) image sensor, or other sensors.

Figures 3, 4:
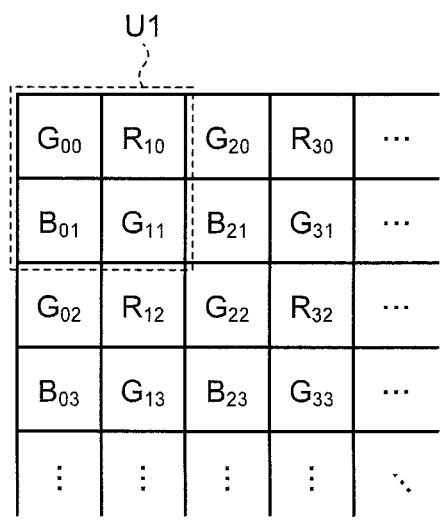
FIG. 3 is a schematic diagram illustrating a configuration of pixels according to the embodiment of the present invention.
FIG. 4 is a schematic diagram illustrating an exemplary configuration of a color filter according to the embodiment of the present invention.

FIG. 3 is a schematic diagram illustrating a configuration of pixels of the image sensor 202. In the image sensor 202, the plurality of pixels for receiving light from the imaging optical system 201 is arranged in a matrix form. The image sensor 202 further generates an electric signal (also referred to as an image signal) by performing photoelectric conversion on light received by each of the pixels. This electric signal includes a pixel value (luminance value) of each of the pixels, positional information of the pixels, or other information. In FIG. 3, a pixel arranged in a column i and a row j is denoted as pixel $P_{ij}$ (where i and j are natural numbers including zero).

The image sensor 202 includes a color filter 202a provided between the imaging optical system 201 and the image sensor 202 and having a plurality of filters that each transmit light of a wavelength band separately set to each of the filters. The color filter 202a is included on a light-receiving surface of the image sensor 202.

FIG. 4 is a schematic diagram illustrating an exemplary configuration of the color filter 202a. In the color filter 202a, filter units U1, each formed by four filters arranged in a 2×2 matrix form, are disposed in a matrix form corresponding arrangement of a pixel $P_{ij}$. In other words, a filter array of the filter unit U1 is regarded as a basic pattern and that basic pattern is arranged repeatedly in the color filter 202a. A light-receiving surface of each of the pixels is arranged with one filter that passes light of a predetermined wavelength band. Therefore the pixel $P_{ij}$ provided with the filter receives light of the wavelength band passed through the filter. For example, a pixel $P_{ij}$ provided with a filter that passes light of a green wavelength band receives light of the green wavelength band. Hereinbelow, a pixel $P_{ij}$ that receives light of the green wavelength band is referred to as a G pixel. Similarly, a pixel that receives light of a blue wavelength band is referred to as a B pixel and a pixel that receives light of a red wavelength band is referred to as an R pixel.

The filter unit U1 passes light of the blue (B) wavelength band $H_B$, the green (G) wavelength band $H_G$, and the red (R) wavelength band $H_R$. Furthermore, the filter unit U1 is formed by a blue filter (B filter) that passes light of the wavelength band $H_B$, a green filter (G filter) that passes light of the wavelength band $H_G$, a red filter (R filter) that passes light of the wavelength band $H_R$. The two G filters are arranged diagonally while the B filter and the R filter are arranged diagonally, thereby forming a so-called Bayer array. In the filter unit U1, the density of the G filters is higher than the density of the B filters or the R filters. In other words, the density of the G pixels is higher than the density of the B pixels or the R pixels in the image sensor 202. The blue, green, and red wavelength bands $H_B$, $H_G$, and $H_R$ are for example 380 nm to 500 nm, 480 nm to 600 nm, and 580 nm to 650 nm, respectively.

Figure 5:
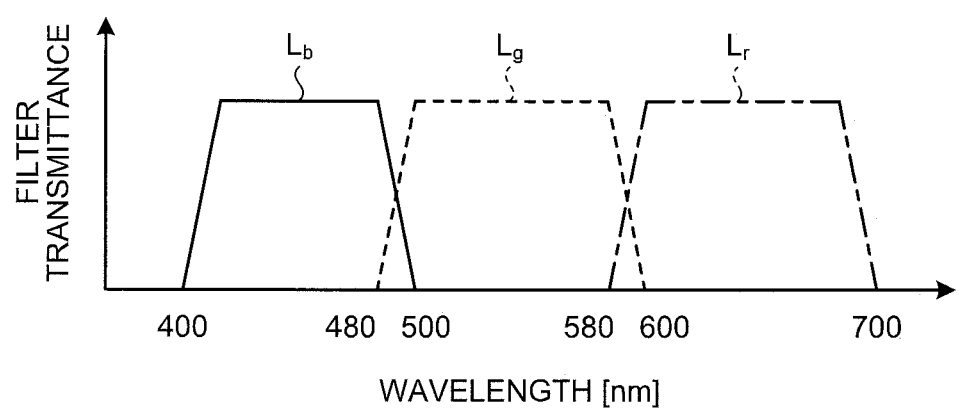
FIG. 5 is a diagram illustrating exemplary characteristics of the respective filters of the color filter according to the embodiment of the present invention as well as the diagram illustrating relationship between the wavelength of light and the transmittance of the respective filters.

FIG. 5 is a diagram illustrating exemplary characteristics of the respective filters of the color filter according to the embodiment as well as a diagram illustrating relationship between the wavelength of light and the transmittance of the respective filters. In FIG. 5, transmittance curves are normalized such that the maximum value of transmittance of each of the filters becomes equivalent. A curve $L_b$ (solid line) illustrated in FIG. 5 represents a transmittance curve of the B filter, a curve $L_g$ (broken line) represents a transmittance curve of the G filter, and a curve $L_r$ (alternate long and short dash line) represents a transmittance curve of the R filter. As illustrated in FIG. 5, the B filter passes light of the wavelength band $H_B$. The G filter passes light of the wavelength band $H_G$. The R filter passes light of the wavelength band $H_R$.

Returning to descriptions on FIGS. 1 and 2, the light guide 203 is formed by a glass fiber or the like and thereby forms a light guiding path of light emitted by the light source unit 3.

The illumination lens 204 is provided to a distal end of the light guide 203 and diffuses light guided by the light guide 203 and emits the light outside the distal end part 24.

The A/D converter 205 performs A/D conversion on the electric signal generated by the image sensor 202 and outputs the converted electric signal to the processor 4. The A/D converter 205 converts the electric signal generated by the image sensor 202 into digital data (image signal) of twelve bits, for example.

The imaging information storage unit 206 stores data including various programs for causing the endoscope 2 to operate, various parameters required for operation of the endoscope 2, an identification information of the endoscope 2. Moreover, the imaging information storage unit 206 includes an identification information storage unit 261 that stores identification information. Identification information includes specific information (ID) of the endoscope 2, year of manufacture, specification information, transmission method, information on filter array of the color filter 202a, etc. The imaging information storage unit 206 is implemented by a flash memory or the like.

Next, a configuration of the light source unit 3 will be described. The light source unit 3 includes an illumination unit 31 and an illumination controller 32.

The illumination unit 31 switches between a plurality of rays of illumination light having different wavelength bands, and emits the illumination light under the control by the illumination controller 32. The illumination unit 31 includes a light source 31a, a light source driver 31b, a switching filter 31c, a driving unit 31d, a driver 31e, and a condenser lens 31f.

The light source 31a emits white illumination light including light of the red, the green, and the blue wavelength bands $H_R$, $H_G$, $H_B$ under control by the illumination controller 32. White illumination light generated by the light source 31a is emitted outside the distal end part 24 via the switching filter 31c, the condenser lens 31f, and the light guide 203. The light source 31a is implemented by a light source that emits white light such as a white LED or a xenon lamp.

The light source driver 31b supplies a current to the light source 31a under control by the illumination controller 32 and thereby causes the light source 31a to emit white illumination light.

The switching filter 31c passes only blue narrow band light and green narrow band light the out of white illumination light emitted by the light source 31a. The switching filter 31c is disposed on an optical path of white illumination light emitted by the light source 31a in a freely insertable and removable manner under control by the illumination controller 32. The switching filter 31c passes only two types of narrow band light when disposed on the optical path of white illumination light. Specifically, the switching filter 31c passes narrow band illumination light formed by light of a narrow band $T_B$ (e.g. 400 nm to 445 nm) included in the wavelength band $H_B$ and light of a narrow band $T_G$ (e.g. 530 nm to 550 nm) included in the wavelength band $H_G$. These narrow bands $T_B$ and $T_G$ are wavelength bands of blue light and green light that are likely to be absorbed by hemoglobin in the blood. The narrow band $T_B$ is only required to include at least 405 nm to 425 nm. Light emitted while limited to these bands is referred to as narrow band illumination light and imaging by the narrow band illumination light is referred to as a narrow band imaging (NBI).

The driving unit 31*d* is formed by a stepping motor, a DC motor, or other motors and causes the switching filter 31*c* to be inserted to or removed from the optical path of the light source 31*a*.

The driver 31*e* supplies a predetermined current to the driving unit 31*d* under control by the illumination controller 32.

The condenser lens 31*f* concentrates white illumination light emitted by the light source 31*a* or narrow band illumination light passed through the switching filter 31*c* and emits the light outside the light source unit 3 (to the light guide 203).

The illumination controller 32 controls the light source driver 31*b* to cause on/off operation of the light source 31*a* and controls the driver 31*e* to cause the switching filter 31*c* to be inserted to or removed from the optical path of the light source 31*a*, thereby controlling the type (band) of illumination light emitted by the illumination unit 31.

Specifically, the illumination controller 32 causes the switching filter 31*c* to be inserted to or removed from the optical path of the light source 31*a* to control switching of illumination light emitted by the illumination unit 31 between white illumination light and narrow band illumination light. In other words, the illumination controller 32 controls switching between the white light imaging (WLI) using white illumination light including light of the wavelength bands $H_B$, $H_G$, and $H_R$ and the narrow band imaging (NBI) using narrow band illumination light formed by light of the narrow bands $T_B$ and $T_G$.

In the white light imaging (WLI) a green component (wavelength band $H_G$) forms a luminance component (first luminance component) while in the narrow band imaging (NBI) a blue component (narrow band $T_B$) forms a luminance component (second luminance component). A luminance component in the present invention refers to a color component forming the main component of a luminance signal in an XYZ colorimetric system for example, which will be described later. For example in the white light imaging, a green component that has the highest relative luminosity factor to human eyes and clearly depicts blood vessels or gland duct structures of a living body forms a luminance component. Meanwhile, in the narrow band light imaging, a selected luminance component is different depending on an object. There may be cases where a green component is selected like in the white light imaging or cases where a luminance component is different from that in white light imaging. Specifically, representative examples where a blue component or a red component forms a luminance component in the narrow band light imaging include the NBI described above. In this case, a blue component that clearly depicts blood vessels or gland duct structures in a surface layer of a living body forms a luminance component. In the embodiment, a green component is regarded as the luminance component in the white light imaging and a blue component is regarded as the luminance component in the narrow band light imaging.

Figure 6:
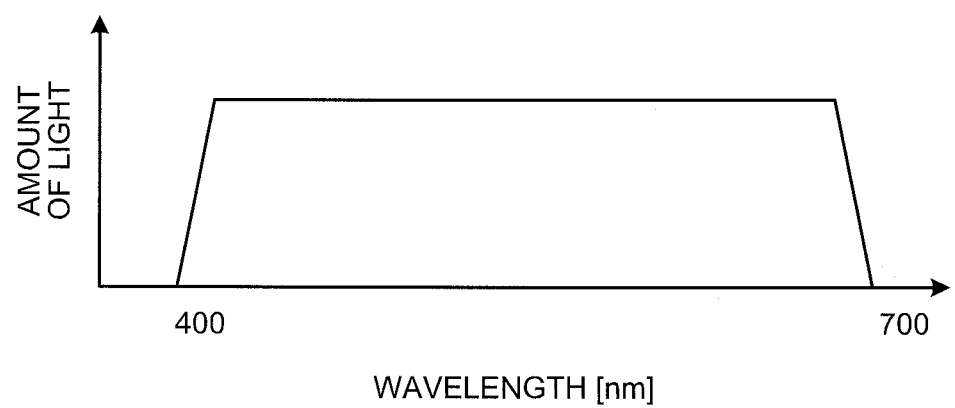
FIG. 6 is a graph illustrating relationship between the wavelength and the amount of light of illumination light emitted by an illumination unit of the endoscope device according to the embodiment of the present invention.
Figure 7:
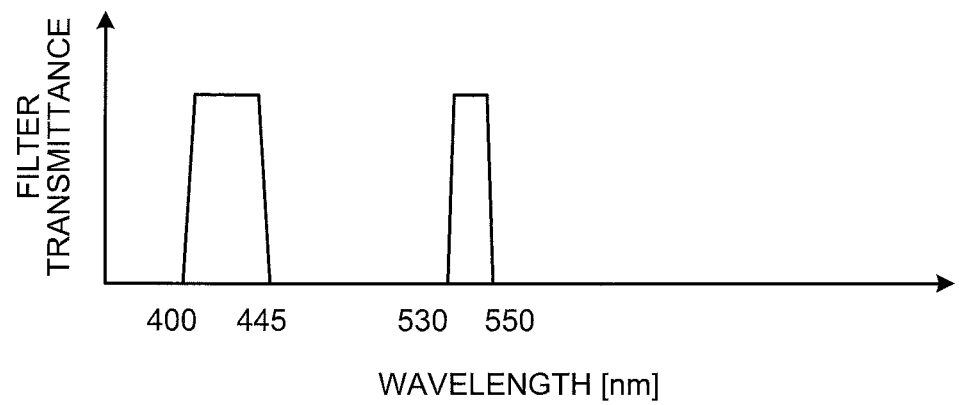
FIG. 7 is a graph illustrating relationship between the wavelength and the transmittance of illumination light through a switching filter included in the illumination unit of the endoscope device according to the embodiment of the present invention.

FIG. 6 is a graph illustrating relationship between the wavelength and the amount of light of illumination light emitted by the illumination unit 31 of the endoscope device 1 according to the embodiment. FIG. 7 is a graph illustrating relationship between the wavelength and the transmittance of illumination light through a switching filter 31*c* included in the illumination unit of the endoscope device 1 according to the embodiment. When the switching filter 31*c* is removed from the optical path of the light source 31*a* by control by the illumination controller 32, the illumination unit 31 emits white illumination light including light of the wavelength bands $H_B$, $H_G$, and $H_R$ (see FIG. 6). Contrary to this, when the switching filter 31*c* is inserted to the optical path of the light source 31*a* by control by the illumination controller 32, the illumination unit 31 emits narrow band illumination light including light of the narrow bands $T_B$ and $T_G$ (see FIG. 7).

Next, a configuration of the processor 4 will be described. The processor 4 includes an image processing unit 41, an input unit 42, a storage unit 43, and a control unit 44.

The image processing unit 41 executes predetermined image processing on the basis of the imaging signal from the endoscope 2 (A/D converter 205) to generate a display image signal to be displayed by the display unit 5. The image processing unit 41 includes a motion detection image generating processing unit 411, a motion detection processing unit 412, a noise reduction processing unit 413, a frame memory 414, a demosaicking processing unit 415, and a display image generation processing unit 416.

The motion detection image generating processing unit 411 performs conversion processing on an unsynchronized image (current image) output from the A/D converter 205 and a previous image held in the frame memory 414 and thereby generates a motion detection image. The conversion processing will be described later. The previous image mentioned here refers to an image after noise reduction processing that has acquired immediately before an image of the latest frame (current image), such as an image one frame before the latest frame. The motion detection image generating processing unit 411 acquires imaging mode information on an imaging method from the control unit 44 and performs conversion processing according to the imaging method. The conversion processing according to the embodiment refers to averaging processing of pixel values of pixels included in a group of a plurality of pixels having different color filters while allowing weighting of a pixel value of a pixel having a filter transmitting light of a luminance component of a captured image (current image or previous image) in the white light imaging to be larger than or equal to weighting of a pixel value of a pixel having another type of filter when illumination light of the white light imaging is used and weighting of a pixel value of a pixel having a filter transmitting light of a luminance component of a captured image in the narrow band imaging to be larger than or equal to weighting of a pixel value of a pixel having another type of filter when the narrow band imaging is used.

The motion detection processing unit 412 detects motion in an image as a motion vector using the motion detection image generated by the motion detection image generating processing unit 411. In other words, the motion detection processing unit 412 detects motion in images between motion detection images having different imaging timings in a time series as a motion vector.

The noise reduction processing unit 413 reduces a noise component of the current image (imaging signal) according to the detection result by the motion detection processing unit 412 and weighted averaging processing between images using the current image and a previous image. The previous image is acquired by outputting the previous image stored in the frame memory 414. The noise reduction processing unit 413 further outputs the current image after the noise reduction processing to the frame memory 414.

The frame memory 414 stores image information of one frame forming one image (unsynchronized image). Specifically, the frame memory 414 stores information of the unsynchronized image after the noise reduction processing by the noise reduction processing unit 413. When a new unsynchronized image is generated by the noise reduction processing unit 413, the frame memory 414 is updated with information on the newly-generated unsynchronized image. An unsynchronized image of a plurality of frames may be stored. The frame memory 414 may be implemented by a semiconductor memory such as a video random access memory (VRAM) or may be implemented by a part of a storage area of the storage unit 43.

The demosaicking processing unit 415 determines an interpolation direction from correlation of color information (pixel values) of a plurality of pixels based on the imaging signal after the noise reduction processing by the noise reduction processing unit 413 for example and performs interpolation based on color information of pixels aligned in the determined interpolation direction, thereby generating a color image signal.

The display image generation processing unit 416 performs color conversion processing on the color image signal generated by the demosaicking processing unit 415 into, for example, a color space of sRGB (XYZ colorimetric system) that is a color gamut of the display unit 5 and further performs tone conversion based on predetermined tone conversion characteristics, enlargement processing, structure enhancing processing of structures such as capillaries or a mucosal fine pattern in the mucosal surface layer, or other processing. After performing predetermined processing, the display image generation processing unit 416 outputs the signal after the processing to the display unit 5 as a display image signal for display.

Apart from the demosaicking processing described above, the image processing unit 41 performs OB clamp processing, gain adjustment processing, or other processing. In OB clamp processing, an electric signal input from the endoscope 2 (A/D converter 205) is performed with processing to correct an offset amount of a black level. In gain adjustment processing, brightness level adjustment is performed on the image signal after the demosaicking processing.

The input unit 42 is an interface for a user to perform input to the processor 4. The input unit 42 includes: a power switch for turning on/off of power; a mode switching button for switching between a shooting mode and other various modes; and an illumination light switching button for switching illumination light (imaging method) of the light source unit 3.

The storage unit 43 stores data including various programs for causing the endoscope device 1 to operate, and various parameters required for operation of the endoscope device 1. The storage unit 43 may store information related to the endoscope 2, for example a relational table of identification information (ID) of the endoscope 2 and information on filter arrangement of the color filter 202a. The storage unit 43 is implemented by a semiconductor memory such as a flash memory or a dynamic random access memory (DRAM).

The control unit 44 is configured by a CPU or the like. The control unit 44 performs driving control of the respective components including the endoscope 2 and the light source unit 3 as well as input and output control of information with the respective components. The control unit 44 transmits, to the endoscope 2 via a predetermined signal wire, setting data for imaging control (e.g. pixels to be read) recorded in the storage unit 43, a timing signal of an imaging timing, or other data. The control unit 44 outputs color filter information (identification information) acquired via the imaging information storage unit 206, imaging mode information on a control mode (imaging mode) corresponding to an imaging method currently employed, or other information to the image processing unit 41 and outputs information on arrangement of the switching filter 31c to the light source unit 3 based on the color filter information.

Next, the display unit 5 will be described. The display unit 5 receives the display image signal generated by the processor 4 via a video cable and displays an in-vivo image corresponding to the display image signal. The display unit 5 is configured by liquid crystal or organic electroluminescence (EL).

Subsequently, signal processing performed by the respective units the processor 4 of the endoscope device 1 will be described with reference to the drawings. FIGS. 8 to 16 are diagrams explaining motion detection image generating processing performed by the motion detection image generating processing unit 411 of the endoscope device 1 according to the embodiment of the present invention.

Motion Detection Image Generating Processing in WLI Mode

Figure 8:
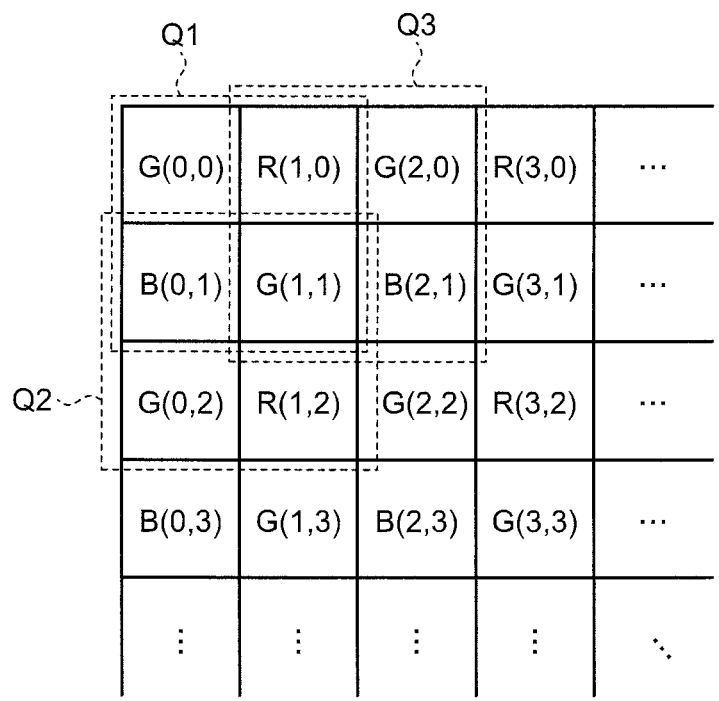
FIG. 8 is a diagram explaining motion detection image generating processing performed by a motion detection image generating processing unit of the endoscope device according to the embodiment of the present invention.

The motion detection image generating processing unit 411 performs averaging processing of four pixel values in an averaging target area which is a group of four pixels in the current image (for example, averaging target areas Q1, Q2, and Q3 illustrated in FIG. 8) where a coordinate of a pixel of interest (pixel $P_{ij}$) is denoted by (x, y) and thereby generates a signal value Y (x, y) of a motion detection image (see FIG. 9). For example, a signal value Y(0, 0) for generating a motion detection image corresponding to a signal value G(0, 0) of a pixel $G_{00}$ is generated by the averaging target area Q1. A signal value Y(0, 1) for generating a motion detection image corresponding to a signal value B(0, 1) of a pixel $B_{01}$ is generated by the averaging target area Q2. A signal value Y(1, 0) for generating a motion detection image corresponding to a signal value R(1, 0) of a pixel $R_{10}$ is generated by the averaging target area Q3. When there is no adjacent pixels, pixels at positions after turning back are used as the averaging target area. Specifically, the motion detection image generating processing unit 411 calculates signals $Y_{00}$ and $Y_{01}$ of a motion detection image according to the following formulae (1) and (2) (the same applies to other coordinates).

$$Y(0, 0) = \frac{1}{4}\{G(0, 0) + R(1, 0) + B(0, 1) + G(1, 1)\} \qquad (1)$$

$$Y(0, 1) = \frac{1}{4}\{B(0, 1) + G(1, 1) + G(0, 2) + R(1, 2)\} \qquad (2)$$

A phase (centroid on FIG. 8) of each of the signal values Y(x, y) generated thereupon is shifted by half a pixel in both the horizontal direction and the vertical direction from the central position of a pixel corresponding thereto (for example, the pixel $G_{00}$ in the case of the signal value Y(0, 0)); however, the phases are arranged uniformly. For example, a phase of a signal value Y(x, y) corresponding to the signal value G(0, 0) is S11. A phase of a signal value Y(0, 1) corresponding to the signal value B(0, 1) is S12 and a phase of a signal value Y(1, 0) corresponding to the signal value R(1, 0) is S13 (see FIG. 10). Moreover, a ratio among RGB signals forming a signal value Y(k, 1) is R:G:B=1:2:1 where a ratio of G signals is high (weight of the G signal is large).

In this manner, the WLI mode has characteristics that biological structures are depicted by the G signal (signal of the luminance component of the WLI) and thus a ratio of signal values of the G component is raised and thereby a signal value Y is generated such that phases become uniform.

Motion Detection Image Generating Processing in NBI Mode

Figure 11:
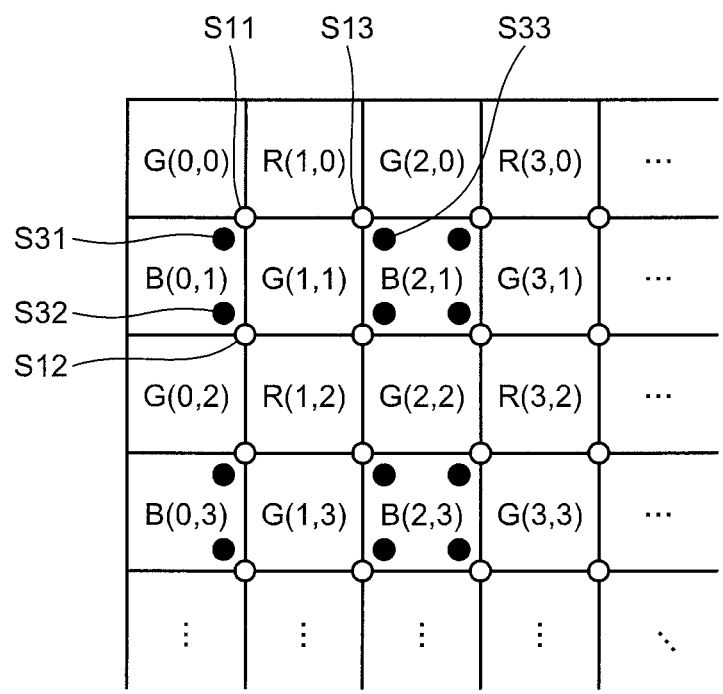
FIG. 11 is a diagram explaining motion detection image generating processing performed by the motion detection image generating processing unit of the endoscope device according to the embodiment of the present invention.

The NBI mode has characteristics that biological structures are depicted by the B signal (signal of the luminance component of the NBI) and using the method for the WLI mode as described above deteriorates an accuracy of motion detection processing since a ratio of B signals included in a Y signal is low. Moreover, no R component is present in narrow band light in the embodiment and a signal value R(1, 0) equals zero. Thus, as illustrated in FIG. 11, a phase of a signal value Y(0, 0) is S31, a phase of a signal value Y(0, 1) is S32, and a phase of a signal value Y(1, 0) is S33, thereby resulting in ununiform phases (black dots in FIG. 11) (shifted phases) at large. Furthermore when an object is moving, an edge shape is deformed between images due to an influence of shifted phases, thereby resulting in a reduced accuracy of motion detection processing. More specifically, of a signal value G(x, y) and a signal value B(x, y) forming the signal value Y(x, y), a phase of the signal value B(x, y) becomes ununiform and thus an accuracy of motion detection processing is reduced. FIGS. 12A and 12B are diagram explaining motion detection image generating processing performed by the motion detection image generating processing unit of the endoscope device according to the embodiment. FIG. 12A illustrates a phase Sg1 of a G signal at a signal value Y(1, 0) and a phase Sb1 of a B signal at a signal value Y(1, 0). FIG. 12B illustrates a phase Sg2 of a G signal at a signal value Y(2, 0) and a phase Sb2 of a B signal at a signal value Y(2, 0). As illustrated in FIGS. 12A and 12B, the phases Sg1 and Sg2 of the G signal vary between the signal value Y(1, 0) and the signal value Y(2, 0) while the phases Sb1 and Sb2 of the B signal do not vary.

In this manner, employing the motion detection image generating processing of the WLI mode to the NBI mode results in the following situations.

1. A ratio of B signals depicting biological structures in the surface layer of a living body is small.
2. Phases of a motion detection image become ununiform.

In order to address the above situations 1 and 2, the motion detection image generating processing unit 411 generates a signal value Y(x, y) using the following formula (3) in the NBI mode. A signal value R(x, y) is not used since the value becomes zero. A coefficient for a signal value $B_{tmp}(x, y)$ is multiplied (2 in formula (3)) is a weighting value for weighting a B component that is a luminance component.

$$Y(x, y) = \frac{1}{3}\{2 \times B_{tmp}(x, y) + G_{tmp}(x, y)\} \tag{3}$$

Specifically, when a signal value Y(0, 1) for generating a motion detection image corresponding to a signal value B(0, 1) of a pixel $B_{21}$ is generated, the motion detection image generating processing unit 411 generates signal values $B_{tmp}$(0, 1) and $G_{tmp}$(0, 1) by the following formulae (4) and (5), respectively, based on signal values of five pixels in an averaging target area Q11 illustrated in FIG. 13 and thereafter generates the signal value Y(0, 1) by formula (3). A phase of the signal value Y(0, 1) is S21 illustrated in FIG. 13.

$$B_{tmp}(0, 1) = \frac{1}{2}B(0, 1) + \frac{1}{4}\{B(2, 1) + B(0, 3)\} \tag{4}$$

$$G_{tmp}(0, 1) = \frac{1}{2}\{G(1, 1) + G(0, 2)\} \tag{5}$$

Moreover, when a signal value Y(2, 1) for generating a motion detection image corresponding to a signal value B(2, 1) of a pixel $B_{21}$ is generated, the motion detection image generating processing unit 411 generates signal values $B_{tmp}$(2, 1) and $G_{tmp}$(2, 1) by the following formulae (6) and (7), respectively, based on signal values of five pixels in an averaging target area Q12 illustrated in FIG. 14 and thereafter generates the signal value Y(2, 1) by formula (3). A phase of the signal value Y(2, 1) is S22 illustrated in FIG. 14.

$$B_{tmp}(2, 1) = \frac{1}{2}B(2, 1) + \frac{1}{4}\{B(0, 1) + B(2, 3)\} \tag{6}$$

$$G_{tmp}(2, 1) = \frac{1}{2}\{G(1, 1) + G(2, 2)\} \tag{7}$$

In order to generate a signal value Y(0, 3) for generating a motion detection image corresponding to a signal value B(0, 3) of a pixel $B_{03}$, the motion detection image generating processing unit 411 generates signal values $B_{tmp}$(0, 3) and $G_{tmp}$(0, 3) by the following formulae (8) and (9), respectively, based on signal values of five pixels in an averaging target area Q13 illustrated in FIG. 15 and thereafter generates the signal value Y(0, 3) by formula (3). A phase of the signal value Y(0, 3) is S23 illustrated in FIG. 15.

$$B_{tmp}(0, 3) = \frac{1}{2}B(0, 3) + \frac{1}{4}\{B(0, 1) + B(2, 3)\} \tag{8}$$

$$G_{tmp}(0, 3) = \frac{1}{2}\{G(0, 2) + G(1, 3)\} \tag{9}$$

Moreover, when a signal value Y(2, 3) for generating a motion detection image corresponding to a signal value B(2, 3) of a pixel $B_{23}$ is generated, the motion detection image generating processing unit 411 generates signal values $B_{tmp}$(2, 3) and $G_{tmp}$(2, 3) by the following formulae (10) and (11), respectively, based on signal values of five pixels in an averaging target area Q14 illustrated in FIG. 16 and thereafter generates the signal value Y(2, 3) by formula (3). A phase of the signal value Y(2, 3) is S24 illustrated in FIG. 16.

$$B_{tmp}(2, 3) = \frac{1}{2}B(2, 3) + \frac{1}{4}\{B(2, 1) + B(0, 3)\} \tag{10}$$

$$G_{tmp}(2, 3) = \frac{1}{2}\{G(2, 2) + G(1, 3)\} \tag{11}$$

Figure 17:
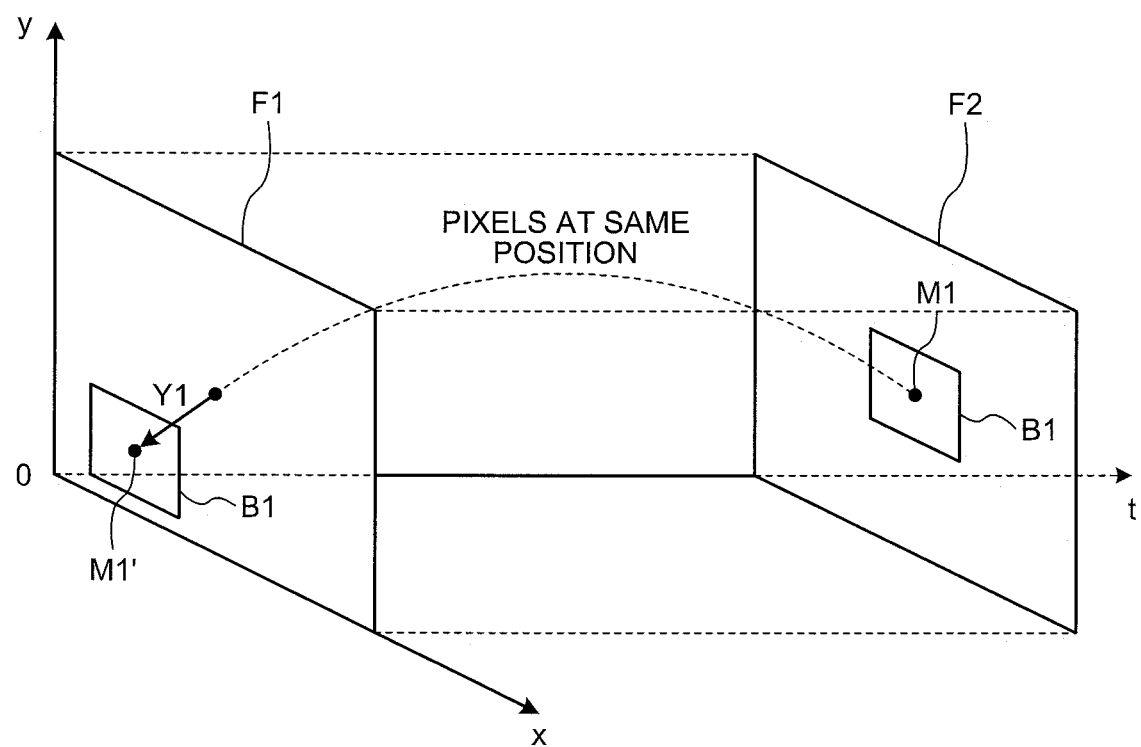
FIG. 17 is a diagram schematically explaining motion between images at different imaging timings captured by a motion detection processing unit of the endoscope device according to the embodiment of the present invention.

The NBI mode has characteristics that biological structures are depicted by the B signal (signal of the luminance component of the NBI) and thus using a pixel generating a signal value Y and a plurality of B pixels and a G pixel in the proximity thereof allows for generating a motion detection image with uniform phases. Specifically, using signal values in an averaging target area including three B pixels and two G pixels out of pixels in a proximity in the horizontal direction and the vertical direction from a pixel position, which generates a signal value Y, as a reference allows for generating a motion detection image with uniform phases. In the example described above, calculation of a signal value Y at a B pixel position has been explained. It is preferable that calculation is performed in a similar manner also with a G pixel position. In this manner, generating a signal value Y(x, y) by signal values in an averaging target area having been set such that a ratio of B signal becomes high and allowing the phases of the signal values Y(x, y) to be uniform improve an accuracy of motion detection processing. A motion detection image with uniform phases may be generated by using a pixel generating a signal value Y and a plurality of G pixels in the proximity thereof in the WLI mode and by using a pixel generating a signal value Y and a plurality of B pixels in the proximity thereof in the NBI mode Next, processing performed by the motion detection processing unit 412 and the noise reduction processing unit 413 will be described. FIG. 17 is a diagram schematically explaining motion between images at different imaging timings captured by the motion detection processing unit 412 of the endoscope device 1 according to the embodiment of the present invention. As illustrated in FIG. 17, the motion detection processing unit 412 detects, as a motion vector by a known block matching method using a block B1 as a template, an image motion amount Y1 between a first motion detection image F1 and a second motion detection image F2 using the first motion detection image F1 based on a previous image and the second motion detection image F2 based on the current image to be processed. The first motion detection image F1 and the second motion detection image F2 are images based on imaging signals of two frames continuous in a time series.

The motion detection processing unit 412 detects a motion vector for each pixel (signal value Y) from the motion detection image generated by the motion detection image generating processing unit 411 using the block matching method. Hereinafter a coordinate of a pixel M1 is denoted as (x, y) and an x component and a y component of a motion vector at the coordinate (x, y) is denoted as Vx(x, y) and Vy(x, y), respectively. When a coordinate of a pixel M1' in the first motion detection image F1 is denoted as (x', y'), x' and y' are defined by the following formulae (12) and (13), respectively. A block matching processing unit 412b outputs detected motion vector information (including positions of the pixels M1 and M1') to the noise reduction processing unit 413.

$$x'=x+Vx(x,y) \quad (12)$$

$$y'=y+Vy(x,y) \quad (13)$$

The noise reduction processing unit 413 reduces noise in the current image by weighted averaging processing between the current image and a previous image. Hereinafter, a signal after noise reduction processing at a pixel of interest, for example pixel M1 (coordinate (x, y)), is denoted as Inr(x, y). The noise reduction processing unit 413 refers to motion vector information, determines whether a reference pixel corresponding to the pixel of interest is of the same color, and executes processing different between the cases where the pixels are of the same color and in different colors. The noise reduction processing unit 413 refers to information of a previous image stored in the frame memory 414, for example, acquires information (signal value or color information of transmitted light) of the pixel M1' (coordinate (x', y')) as the reference pixel corresponding to the pixel M1, and determines whether the pixel M1' is of the same color as that of the pixel M1.

1) When the Pixel of Interest and the Reference Pixel are of the Same Color

When the pixel of interest and the reference pixel are of the same color (the pixels receive light of the same color component), the noise reduction processing unit 413 performs weighted averaging processing while using a pixel in each of an unsynchronized image and a cyclic pixel using the following formula (14) and thereby generates a signal Inr(x, y).

$$Inr(x,y)=\text{coef}\times I(x,y)+(1-\text{coef})\times I'(x',y') \quad (14)$$

Where, I(x, y): signal value of the pixel of interest in the current image, and

I'(x', y): signal value of the reference pixel in a previous image.

A coefficient coef is any real number satisfying 0<coef<1. The coefficient coef may be set in advance as a predetermined value or may be set at any value via the input unit 42 by a user.

2) When the Pixel of Interest and the Reference Pixel are in Different Colors

When the pixel of interest and the reference pixel are in different colors (the pixels receive light of different color components), the noise reduction processing unit 413 interpolates a signal value to the reference pixel of the previous image from pixels of the same color surrounding therearound. The noise reduction processing unit 413 generates the signal Inr(x, y) after noise reduction processing using the following formula (15), for example.

$$Inr(x, y) = coef \times I(x, y) + (1 - coef) \times \frac{\sum_{i=-K}^{K} \sum_{j=-K}^{K} w(x' + i, y' + j) \times I'(x' + i, y' + j)}{\sum_{i=-K}^{K} \sum_{j=-K}^{K} w(x' + i, y' + j)} \quad (15)$$

Where w(x'+i, y'+j) equals 1 when I(x, y) and I' (x'+i, y'+j) are signal values of the same color component, and w(x'+i, y'+j) equals 0 when I(x, y) and I'(x'+i, y'+j) are signal values of different color components.

In formula (15), w(x'+i, y'+j) is a function for extracting the same color component and equals 1 when a surrounding pixel (x'+i, y'+j) is of the same color as that of the pixel of interest (x, y) and equals zero when they are of different colors. K is a parameter for setting the size of a surrounding area to be referred to. The parameter K is set at 1 (K=1) for a G pixel and set at 2 (K=2) for a B pixel or an R pixel. K=2 may be set for a G pixel and K=4 may be set for a B pixel or an R pixel.

Thereafter, the demosaicking processing unit 415 performs interpolation processing based on a signal (signal Inr(x, y)) performed with noise reduction processing by the noise reduction processing unit 413 and thereby generates a color image signal. The demosaicking processing unit 415 determines an interpolation direction from correlation of color information (pixel values) of a plurality of pixels based on a signal value of a luminance component corresponding to an imaging method for example, performs interpolation based on color information of pixels aligned in the determined interpolation direction, and thereby generates a color image signal. Alternatively, as another method, known bi-cubic interpolation may be employed.

The demosaicking processing unit 415 performs interpolation processing and thereby generates a color image signal including a color image (synchronized image) assigned with a signal value including RGB components or GB components for each pixel position. The demosaicking processing unit 415 allocates a signal of the luminance component or a color component to each of RGB channels. Relationships between a channel and a signal in the imaging methods (WLI/NBI) are shown below. In the embodiment, a signal of the luminance component is allocated to the G channel.

|  | WLI | NBI |
| --- | --- | --- |
| R channel | R signal | G signal |
| G channel | G signal | B signal |
| B channel | B signal | B signal |

Figure 18:
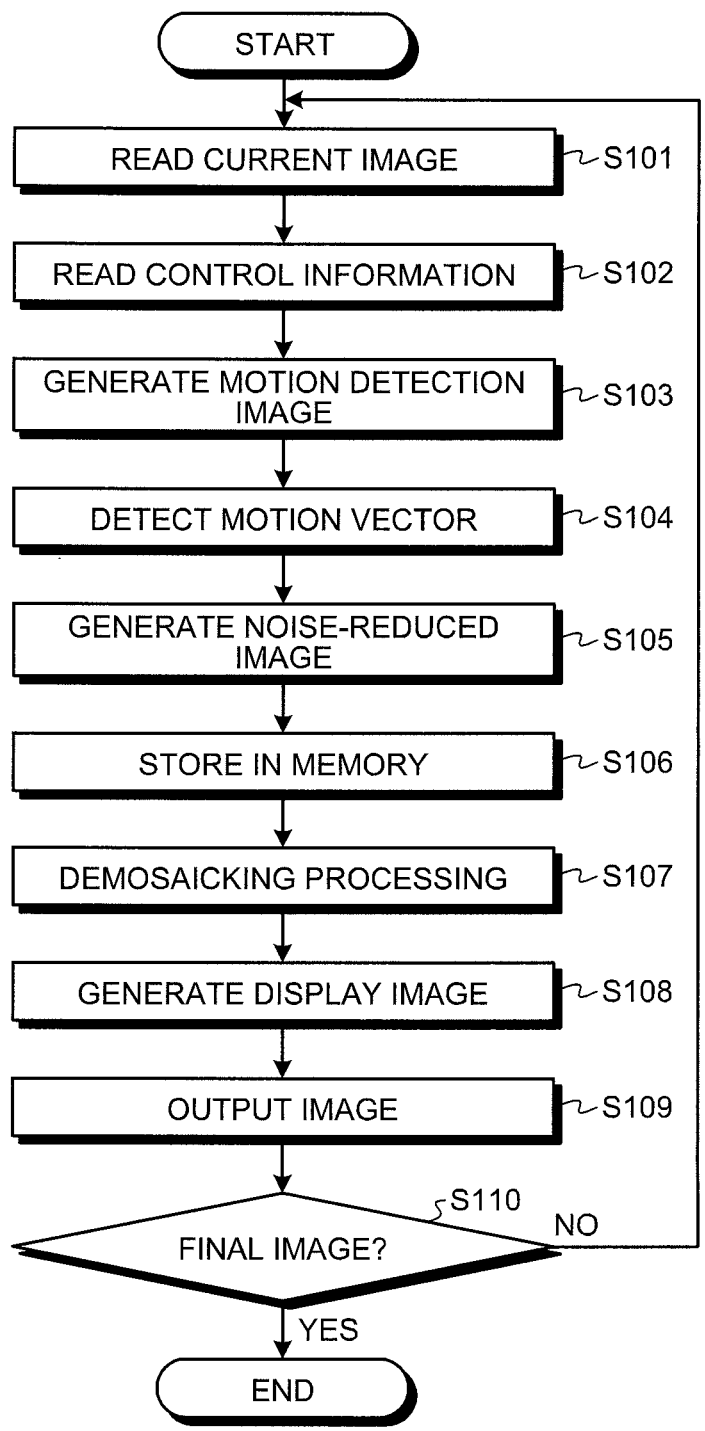
FIG. 18 is a flowchart illustrating signal processing performed by a processor of the endoscope device according to the embodiment of the present invention.

Subsequently, signal processing performed by the processor 4 having the configuration described above will be described with reference to the drawings. FIG. 18 is a flowchart illustrating signal processing performed by the processor 4 of the endoscope device 1 according to the embodiment. The control unit 44 acquires an electric signal from the endoscope 2 and then reads the current image (unsynchronized image) included in the electric signal (step S101). The electric signal from the endoscope 2 is generated by the image sensor 202 and includes unsynchronized image data converted into a digital signal by the A/D converter 205.

After reading the current image, the control unit 44 refers to the identification information storage unit 261 to acquire control information (for example information related to illumination light (imaging method) or array information of the color filter 202a) and outputs the control information to the motion detection image generating processing unit 411 and the demosaicking processing unit 415 (step S102).

The motion detection image generating processing unit 411 determines by which imaging method of the acquired white light imaging (WLI) and the narrow band imaging (NBI) the electric signal (read unsynchronized image) is generated based on the control information (which imaging method is set) and generates a motion detection image based on the determination (step S103: motion detection image generation step). The motion detection image generating processing unit 411 generates a motion detection image based on the current image and a previous image stored in the frame memory 414 and outputs the generated motion detection image to the motion detection processing unit 412 and the frame memory 414.

When acquiring the motion detection image from the motion detection image generating processing unit 411, the motion detection processing unit 412 detects a motion vector based on the motion detection image corresponding to the current image and the motion detection image corresponding to the previous image (S104: motion detection processing step). The motion detection processing unit 412 outputs the detected motion vector to the noise reduction processing unit 413.

The noise reduction processing unit 413 performs noise reduction processing on the electric signal (current image read in step S101) using the current image, the previous image, and the motion vector detected by the motion detection processing unit 412 (step S105). The electric signal (unsynchronized image) after noise reduction processing generated in the present step S105 is output to the demosaicking processing unit 415 and is also stored (updated) in the frame memory 414 as a previous image (step S106).

When input with the electric signal after noise reduction processing from the noise reduction processing unit 413, the demosaicking processing unit 415 performs demosaicking processing based on the electric signal (step S107). The demosaicking processing unit 415 interpolates a luminance component at a pixel position of a color component other than the luminance component and thereby generates an image signal that forms one piece of image where each pixel has a pixel value or an interpolated value of the luminance component. Thereafter, the demosaicking processing unit 415 generates an image signal that forms one piece of image having a pixel value or an interpolated value of each of the RGB color components based on a pixel value and an interpolated value of the luminance component as well as a pixel value of a pixel of a color component other than the luminance component. The demosaicking processing unit 415 then generates a color image signal forming a color image using each image signal of each of the color components. The demosaicking processing unit 415 generates a color image signal using an image signal of a red component, a green component, and a blue component in the WLI mode and generates a color image signal using an image signal of a green component and a blue component in the NBI mode.

After the color image signal is generated by the demosaicking processing unit 415, the display image generation processing unit 416 performs color conversion processing on a color space of sRGB (XYZ colorimetric system), for example, that is a color gamut of the display unit 5 and thereby generates a display image signal for display by performing tone conversion based on predetermined tone conversion characteristics, enlargement processing, or other processing (step S108). After performing predetermined processing, the display image generation processing unit 416 outputs the signal to the display unit 5 as a display image signal.

When the display image signal is generated by the display image generation processing unit 416, image display processing is performed corresponding to the display image signal (step S109). The image display processing allows an image corresponding to the display image signal to be displayed on the display unit 5.

After the processing of generating the display image signal and the image display processing by the display image generation processing unit 416, the control unit 44 determines whether the image is the final image (step S110). The control unit 44 terminates the processing when the series of processing is completed on all images (step S110: Yes) and, when an unprocessed image still remains, the control unit 44 transfers to step S101 and continues similar processing (step S110: No).

In the embodiment, each element constituting the processor 4 is configured by hardware to perform processing; however, the CPU may perform processing of the respective units and the signal processing described above may be implemented by software through execution of a program by the CPU. For example, the signal processing may be implemented by the CPU executing the software described above on an image having been acquired in advance by an image sensor such as a capsule endoscope. Moreover, a part of processing performed by the respective units may be configured by software. In this case, the CPU executes signal processing according to the flowchart described above.

According to the embodiment described above, the motion detection image generating processing unit 411 generates a signal value Y with uniform phases regardless of imaging methods (WLI mode and NBI mode) and the motion detection processing unit 412 detects a motion vector based on the signal value Y. Therefore, a motion vector can be detected with a high accuracy in both the white light imaging and the narrow band imaging. Specifically, the motion detection image generating processing unit 411 generates, in the WLI mode, a signal value Y based on four signal values in an averaging target area where a ratio of signal values of the G component as the luminance component is high and generates, in the NBI mode, a signal value Y by setting an averaging target area such that a ratio of signals of the B component as the luminance component becomes high or by weighting a signal value. Moreover, phases of the signal values Y becomes uniform. Therefore, the subsequent motion vector detecting processing can be performed with a high accuracy.

First Modification of Embodiment

In the embodiment described above, the motion vector detecting processing and the noise reduction processing are performed on the current image output from the A/D converter 205; however, the present invention is not limited thereto. In the first modification, the motion vector detecting processing and the noise reduction processing is performed on a color image signal after interpolation processing. In this case, the current image acquired by an A/D converter 205 is output to a demosaicking processing unit 415. A color image signal generated by the demosaicking processing unit 415 is output to a motion detection image generating processing unit 411 and a noise reduction processing unit 413.

The motion detection image generating processing unit 411 generates a motion detection image using the following formula (16) or (17) depending on the imaging method. Signal values Ri(x, y), Gi(x, y), and Bi(x, y) in formulae (16) and (17) are signal values of a color component generated by interpolation at a pixel position corresponding to a signal value Y(x, y). In formulae (16) and (17), a signal value of the luminance component of each of the imaging methods is weighted.

In WLI Mode $$Y(x, y) = \frac{1}{4}\{Ri(x, y) + 2 \times Gi(x, y) + Bi(x, y)\} \quad (16)$$

<In NBI Mode>

$$Y(x, y) = \frac{1}{3}\{2 \times Bi(x, y) + Gi(x, y)\} \quad (17)$$

The noise reduction processing unit 413 is only required to generate a noise-reduced image using the above formula (14) and to output the image to the display image generation processing unit 416. According to this method, the interpolation processing shown by the above formula (15) is not required upon noise reduction processing, thereby allowing for reducing calculation cost.

Second Modification of Embodiment

In the embodiment described above, the signal value Y (motion detection image) is generated by a simple arithmetic mean of four pixels in the WLI mode; however, the present invention is not limited thereto. In the second modification, a signal value Y is generated from a weighted average of signal values of the RGB color components. As a weighting value, a predetermined value set in advance may be used or an operator or others may set any value from the input unit 42. In either case, it is preferable that a ratio of signal values of the G component in the signal values Y is 50% or more. For example, a conversion formula shown in the following formula (18) is used for calculating a signal value Y.

$$Y(x,y)=0.21\times R(x,y)+0.72\times G(x,y)+0.07\times B(x,y) \quad (18)$$

In the NBI mode a signal value Y is generated at a ratio of B:G=2:1; however, the present invention is not limited thereto. Also in this case an operator or others may set any value from the input unit 42 (B:G=1:1 or B:G=3:1). It is preferable that a ratio of signal values of the B component is set at 50% or more.

Third Modification of Embodiment

In the embodiment described above, the signal value Y (motion detection image) is generated using the above formulae (4), (6), (8), and (10) in the NBI mode; however, the present invention is not limited thereto. In the third modification, a value $B_{tmp}$ shown in the above formula (3) may be calculated using the following formulae (19) to (22) (signal values of four B pixels surrounding a B pixel of interest are used). Although the B pixels are selected from a pixel area of 3×3 surrounding and including the pixel of interest, B pixels may be selected from a pixel area of 5×5.

$$B_{tmp}(0, 1) = \frac{5}{8}B(0, 1) + \frac{1}{8}\{B(2, 1) + B(0, 3) + B(2, 3)\} \quad (19)$$

$$B_{tmp}(2, 1) = \frac{5}{8}B(2, 1) + \frac{1}{8}\{B(0, 1) + B(2, 3) + B(0, 3)\} \quad (20)$$

$$B_{tmp}(0, 3) = \frac{5}{8}B(0, 3) + \frac{1}{8}\{B(0, 1) + B(2, 3) + B(2, 1)\} \quad (21)$$

$$B_{tmp}(2, 3) = \frac{5}{8}B(2, 3) + \frac{1}{8}\{B(2, 1) + B(0, 3) + B(0, 1)\} \quad (22)$$

Fourth Modification of Embodiment

In the embodiment described above, a motion detection image has the same size as that of the current image and a previous image as illustrated in FIGS. 8 to 10; however, the present invention is not limited thereto. In the fourth modification, a motion detection image downsized to a half of the size of the current image and a previous image in the horizontal direction and the vertical direction is generated. FIGS. 19 to 22 are diagrams explaining motion detection image generating processing performed by a motion detection image generating processing unit 411 of an endoscope device 1 according to the fourth modification of the embodiment of the present invention.

The motion detection image generating processing unit 411 generates a motion detection image using the following formulae (23) to (29) depending on the imaging method where a signal value of the motion detection image is denoted as Ys(x, y).

In WLI Mode

Figure 19:
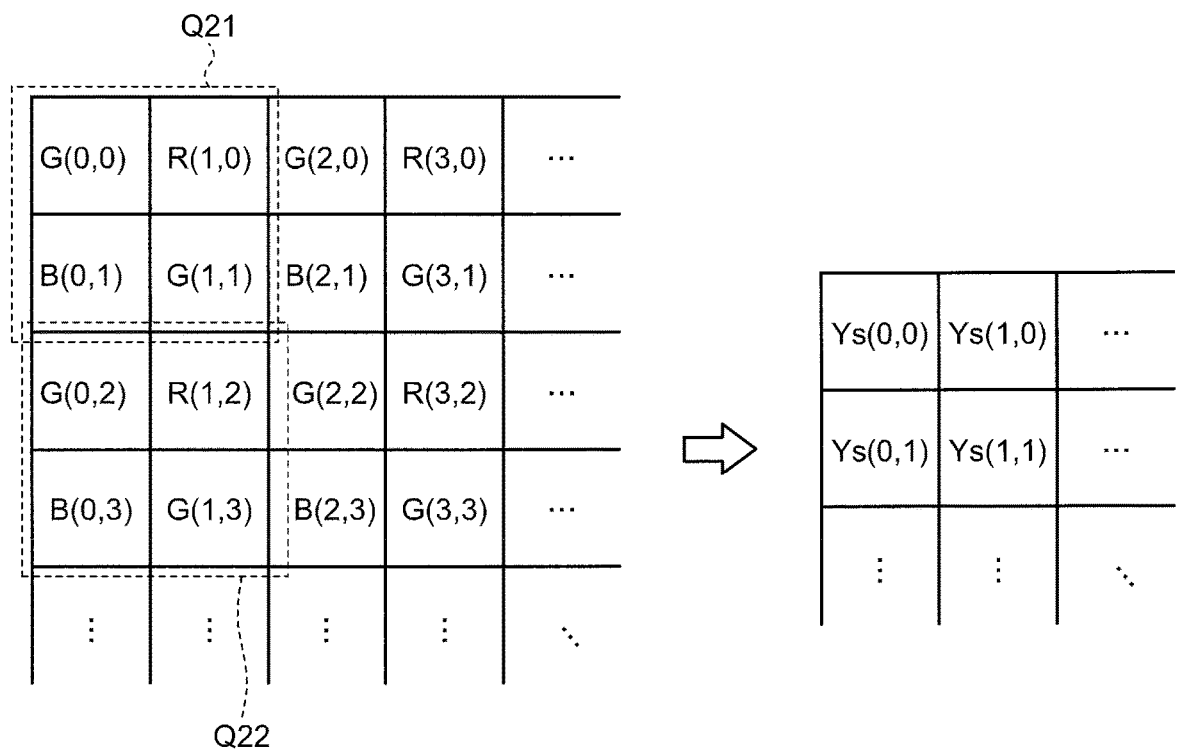
FIG. 19 is a diagram explaining motion detection image generating processing performed by a motion detection image generating processing unit of an endoscope device according to a fourth modification of the embodiment of the present invention.

In the WLI mode, for example, a signal value Ys(x, y) is generated using the following formulae (23) and (24) (see FIG. 19). An averaging target area is set such that a signal value of a pixel is not used for multiple times for example the averaging target areas Q21 and Q22 illustrated in FIG. 19.

$$Ys(0,0)=G(0,0)+R(1,0)+B(0,1)+G(1,1) \qquad (23)$$

$$Ys(0,1)=G(0,2)+R(1,2)+B(0,3)+G(1,3) \qquad (24)$$

In NBI Mode

In the NBI mode, a signal value Ys(x, y) is generated using the following formulae (25) to (29) (see FIG. 20). An averaging target area is set to be formed by nine pixels surrounding and including a B pixel in the center, for example, the averaging target areas Q31 and Q32 illustrated in FIG. 20.

$$Ys(x, y) = \frac{1}{3}\{2 \times B_{tmp2}(x, y) + G_{tmp2}(x, y)\} \qquad (25)$$

Specifically, when a signal value Ys(1, 0) for generating a motion detection image is generated, the motion detection image generating processing unit 411 generates signal values $B_{tmp2}(1, 0)$ and $G_{tmp2}(1, 0)$ by the following formulae (26) and (27), respectively, based on signal values of five pixels (excluding an R pixel) in the averaging target area Q31 illustrated in FIG. 20 and thereafter generates the signal value Ys(1, 0) by the formula (25). A phase of a signal value Ys(1, 0) is S41 illustrated in FIG. 21.

$$B_{tmp2}(1,0)=B(2,1) \qquad (26)$$

$$G_{tmp2}(1, 0) = \frac{1}{4}\{G(2, 0) + G(1, 1) + G(3, 1) + G(2, 2)\} \qquad (27)$$

Specifically, when a signal value Ys(1, 1) for generating a motion detection image is generated, the motion detection image generating processing unit 411 generates signal values $B_{tmp}(1, 1)$ and $G_{tmp}(1, 1)$ by the following formulae (28) and (29), respectively, based on signal values of seven pixels (excluding an R pixel) in the averaging target area Q32 illustrated in FIG. 20 and thereafter generates the signal value Ys(1, 1) by the formula (25). A phase of a signal value Ys(1, 1) is S42 illustrated in FIG. 22.

$$B_{tmp2}(1, 1) = B(2, 3) \qquad (28)$$

$$G_{tmp2}(1, 1) = \frac{1}{4}\{G(2, 2) + G(1, 3) + G(3, 3) + G(2, 4)\} \qquad (29)$$

According to the fourth modification, a motion detection image is downsized and thus calculation cost required for block matching processing by a motion detection processing unit 412 can be reduced (circuit scale can be reduced). In the fourth modification, the motion detection processing unit 412 doubles the size of a detected motion vector (convert into a motion vector in the current image) and thereby outputs to the noise reduction processing unit 413.

Fifth Modification of Embodiment

In the embodiment described above, the image sensor 202 includes, as a basic pattern, a filter unit U1 (see FIG. 4) formed by 2×2 pixels; however, the present invention is not limited thereto. For example, a filter unit formed by 4×4 pixels may be employed. FIG. 23 is a schematic diagram illustrating a configuration of a color filter according to the fifth modification of the embodiment of the present invention. The filter unit U2 illustrated in FIG. 23 includes eight G filters, six B filters, and two R filters arranged such that filters of the same color are not adjacent to each other in the horizontal direction and the vertical direction. Processing of generating a motion detection image with the filter unit U2 will be described below.

In WLI Mode

In the WLI mode, a signal value Y(x, y) of a motion detection image is generated by averaging processing of four pixels for the current image (similarly to FIG. 8). For example, signal values Y(0, 0) and Y(0, 1) of a motion detection image are generated using the above formulae (1) and (2) (similar manner also applied to other coordinates).

In NBI Mode

In the NBI mode, a signal value of an R pixel equals zero and thus is not used as described above. In this case, for example four pixels in the upper left in the filter unit U2 illustrated in FIG. 23 are formed only by G pixels and B pixels without including an R pixel and thus Y(0, 0) is generated by averaging processing of the four pixels as described above with the above formula (1). Meanwhile, in the case of Y(0, 1), four pixels ($B_{21}$, $G_{22}$, $G_{31}$, and $R_{32}$) includes the R pixel and thus it is required to avoid occurrence of a phase shift using the above formulae (4) and (5). Specifically, for example the following formulae (30) to (33) are used. Coordinates allocated to signal values are similar to the above.

* When no R pixel is present in an averaging target area (e.g. in the case of signal value Y(0, 0))

$$Y(0,0)=G(0,0)+B(1,0)+B(0,1)+G(1,1) \qquad (30)$$

* When an R pixel is present in an averaging target area (e.g. in the case of signal value Y(0, 1))

$$Y(x, y) = \frac{1}{3}\{2 \times B_{tmp}(x, y) + G_{tmp}(x, y)\} \qquad (31)$$

$$B_{tmp}(0, 1) = \frac{1}{2}B(0, 1) + \frac{1}{4}\{B(2, 1) + B(0, 3)\} \qquad (32)$$

$$G_{tmp}(0, 1) = \frac{1}{2}\{G(1, 1) + G(0, 2)\} \qquad (33)$$

In the NBI mode, a signal value Y is generated using the above formulae (30) to (33) depending on arrangement of an R pixel.

The color filter 202a according to the embodiment described above is only required to have filter units where the number of G filters transmitting light of the wavelength band $H_G$ is larger than the number of B filters transmitting light of the wavelength band $H_B$ and the number of R filters transmitting light of the wavelength band $H_R$. Thus any arrangement satisfying the above condition may be employed other than the arrangement described above. The filter unit described above has an arrangement of 2×2 or 4×4; however, the arrangement in the filter unit is not limited thereto.

In the embodiment described above, the color filter 202a including the plurality of filters each transmitting light of a predetermined wavelength band is provided on the light-receiving surface of the image sensor 202; however, each of the filters may be separately provided for each pixel of the image sensor 202.

In the embodiment described above, narrow band illumination light is formed by light of the narrow band $T_B$ included in the wavelength band $H_B$ and light of a narrow band $T_G$ included in the wavelength band $H_G$; however, the narrow band illumination light is not limited to these narrow bands. For example, narrow band illumination light may be formed by light of the narrow band $T_R$ included in the wavelength band $H_R$ and light of the narrow band $T_G$ included in the wavelength band $H_G$. Light of the narrow band $T_R$ included in the wavelength band $H_R$ allows for observing blood vessels in the deep layer, for example. A luminance component in the narrow band light imaging in this case is a red component. Similarly to setting an area on the basis of a B pixel as described above, an averaging target area is set on the basis of an R pixel.

The endoscope device 1 according to the embodiment described above switch illumination light emitted from the illumination unit 31 to one of the white illumination light and the narrow band illumination light by inserting or removing the switching filter 31c with respect to white light emitted from one light source 31a; however, switching between two light sources may be employed to emit one of the white illumination light and the narrow band illumination light. As a device for switching between the two light sources to emit one of the white illumination light and the narrow band illumination light, a capsule endoscope may be employed which includes the light source units, a color filter, and an image sensor and configured to be introduced into a subject, for example.

The endoscope device 1 according to the embodiment described above include the A/D converter 205 at the distal end part 24; however, the A/D converter 205 may be included in the processor 4. Furthermore, the configuration related to the image processing may be included in the endoscope 2, a connector connecting the endoscope 2 and the processor 4, or the operating unit 22. The endoscope device 1 described above identify the endoscope 2 connected to the processor 4 using the identification information or other information stored in the identification information storage unit 261; however, an identification unit may be provided to a connection part (connector) between the processor 4 and the endoscope 2. For example, a pin for identification (identification unit) may be included on the endoscope 2 side to identify the endoscope 2 connected to the processor 4.

According to some embodiments, it is possible to detect a motion vector with a high accuracy in any of the white light imaging and the narrow band imaging.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for generating a captured image based on a signal value generated by a plurality of pixels according to one of white illumination light in white light imaging and narrow band illumination light in a narrow band light imaging, the white illumination light including red, green, and blue wavelength bands, the narrow band illumination light being included in one of the red, green, and blue wavelength bands, the image processing apparatus comprising:

a processor configured to:

perform averaging processing on pixel values of pixels included in a group of a plurality of pixels having different color filters to obtain a signal value for generating motion detection images, and generate the motion detection images for detecting motion between captured images at different points in time based on the signal value obtained by the averaging processing in such a way that, in the white light imaging, a weight of a pixel value of a pixel having a filter for passing light of a luminance component of a captured image in the white light imaging is set to be larger than or equal to a weight of a pixel value of a pixel having a different type of filter while in the narrow band imaging, a weight of a pixel value of a pixel having a filter for passing light of a luminance component of a captured image in the narrow band imaging is set to be larger than or equal to a weight of a pixel value of a pixel having a different type of filter; and detect, based on the generated motion detection images, the motion between two of the motion detection images generated based on the captured images at the different points in time.

2. The image processing apparatus according to claim 1, wherein the luminance component in the white light imaging is a green component, the luminance component in the narrow band light imaging is a blue component, and the processor is configured to perform the averaging processing by weighting the pixel value of the green component in the white light imaging, and perform the averaging processing by weighting the pixel value of the blue component in the narrow band light imaging.

3. The image processing apparatus according to claim 1, wherein phases of the signal value for generating the motion detection images based on an arrangement in the group of the plurality of pixels, are uniformly arranged in the motion detection images.

4. The image processing apparatus according to claim 1, wherein the processor is further configured to reduce a noise component included in the captured images based on the detected motion.

5. A method for operating an image processing apparatus for generating a captured image based on a signal value generated by a plurality of pixels according to one of white illumination light in white light imaging and narrow band illumination light in a narrow band light imaging, the white illumination light including red, green, and blue wavelength bands, the narrow band illumination light being included in one of the red, green, and blue wavelength bands, the method comprising:

averaging processing on pixel values of pixels included in a group of a plurality of pixels having different color filters to obtain a signal value for generating motion detection images, and generating the motion detection images for detecting motion between captured images at different points in time based on the signal value obtained by the averaging processing in such a way that, in the white light imaging, a weight of a pixel value of a pixel having a filter for passing light of a luminance component of a captured image in the white light imaging is set to be larger than or equal to a weight of a pixel value of a pixel having a different type of filter while in the narrow band imaging, a weight of a pixel value of a pixel having a filter for passing light of a luminance component of a captured image in the narrow band imaging is set to be larger than or equal to a weight of a pixel value of a pixel having a different type of filter; and detecting, based on the generated motion detection images, the motion between two of the motion detection images generated based on the captured images at the different points in time.

6. A non-transitory computer-readable recording medium with an executable program stored thereon for operating an image processing apparatus for generating a captured image based on a signal value generated by a plurality of pixels according to one of white illumination light in white light imaging and narrow band illumination light in a narrow band light imaging, the white illumination light including red, green, and blue wavelength bands, the narrow band illumination light being included in one of the red, green, and blue wavelength bands, the program causing the image processing apparatus to execute:

performing averaging processing on pixel values of pixels included in a group of a plurality of pixels having different color filters to obtain a signal value for generating motion detection images, and generating the motion detection images for detecting motion between captured images at different points in time based on the signal value obtained by the averaging processing in such a way that, in the white light imaging, a weight of a pixel value of a pixel having a filter for passing light of a luminance component of a captured image in the white light imaging is set to be larger than or equal to a weight of a pixel value of a pixel having a different type of filter while in the narrow band imaging, a weight of a pixel value of a pixel having a filter for passing light of a luminance component of a captured image in the narrow band imaging is set to be larger than or equal to a weight of a pixel value of a pixel having a different type of filter; and detecting, based on the generated motion detection images, the motion between two of the motion detection images generated based on the captured images at the different points in time.

7. An endoscope device for performing white light imaging and narrow band light imaging, the endoscope device comprising:

a light source configured to emit one of white illumination light and narrow band illumination light, the white illumination light including red, green, and blue wavelength bands, the narrow band illumination light including two narrow bands included in one of wavelength bands of luminance components in the white light imaging and the narrow band light imaging;

an image sensor having a plurality of pixels arranged in a matrix form, the plurality of pixels being configured to receive light and perform photoelectric conversion on the received light to generate an electric signal;

a color filter having a plurality of filter units arranged on a light-receiving surface of the image sensor, each of the plurality of filter units including a first filter, a second filter, and a third filter, the first filter being configured to pass light of wavelength bands of a luminance component in the white light imaging and a luminance component in the narrow band light imaging, the second filter being configured to pass light of a wavelength band of the luminance component in the white light imaging, and the third filter being configured to pass light of a wavelength band of the luminance component in the narrow band light imaging; and the image processing apparatus according to claim 1.

* * * * *